United States Patent [19]

Vanlerberghe et al.

[11] Patent Number: 5,164,488
[45] Date of Patent: Nov. 17, 1992

[54] NEW HEMIACETAL COMPOUNDS AND THE APPLICATIONS THEREOF

[75] Inventors: Guy Vanlerberghe, Claye-Souilly; Alexandre Zysman; Henri Sebag, both of Paris, all of France

[73] Assignee: L'Oreal, Paris, France

[21] Appl. No.: 654,517

[22] Filed: Feb. 13, 1991

[30] Foreign Application Priority Data

Jun. 14, 1985 [LU] Luxembourg .......................... 85952

[51] Int. Cl.$^5$ .................... C07K 15/28; C07K 17/02; A61K 9/127; B01J 13/02
[52] U.S. Cl. ................................. 530/391.1; 424/401; 424/450; 424/59; 424/88; 424/94.3; 424/85.91; 424/65; 424/70; 530/391.7; 530/404; 530/405; 530/408; 530/409; 530/810; 428/402.2; 264/4.1; 426/89; 426/662
[58] Field of Search ..................... 264/4.1; 428/402.2; 424/450, 401, 59, 65, 70, 88, 94.3, 85.91; 426/89, 662; 514/21; 530/390, 391, 408, 409, 404, 405, 810

[56] References Cited

U.S. PATENT DOCUMENTS 3,427,248 2/1969 Lamberti et al. .................... 252/117
4,061,869 12/1977 Schwarze et al. .................... 526/1

FOREIGN PATENT DOCUMENTS 1157774 11/1983 Canada .
2631030 1/1978 Fed. Rep. of Germany .
443559 2/1936 United Kingdom .

OTHER PUBLICATIONS

Chem. Abstracts, vol. 73, 1970, pp. 345-346, No. 120262r.
Chem. Abstracts, vol. 72, 1970, p. 329, No. 66306x.
Chem. Abstracts, vol. 106, 1987, p. 609, No. 84580g.
Chem. Abstracts, vol. 63, 1965, No. 2926c.
Chem. Abstracts, vol. 83, 1975, p. 181, No. 61662c.
Chem. Abstracts, vol. 65, 1966, No. 12374f.
Chem. Abstracts, vol. 67, 1967, No. 15186x.
Chem. Abstracts, vol. 91, 1979, No. 118660x.

Japanese Abstracts, JP 54/49322, 1979, as for structure shown in product #DAUC 1305.

Primary Examiner—Christine M. Nucker
Assistant Examiner—Kay Kim
Attorney, Agent, or Firm—Jacobson, Price, Holman & Stern

[57] ABSTRACT

The invention relates to compounds of formula:

$$R\text{-}(O)_u\text{-}A\text{-}(CH_2)_m\overset{\displaystyle O-(CH_2)_q}{\underset{\displaystyle (CH_2)_n\text{-}O\text{-}(CH_2)_p}{<}}\overset{\displaystyle OH}{\underset{\displaystyle H}{>}} \quad (I)$$

in which m, n, p and q are equal to 0 or 1, p being different from q and the sum $m+n+p+q$ being equal to 2, A denotes a nonionic chain arrangement chosen from the groups:

$C_2H_4O_r$ and/or $C_3H_5(OH)O_s$, in which r denotes a number which can assume all integral values between 0 and 5 or a statistical average value between 0 and 20,
s denotes a number which can assume all integral values between 0 and 5 or a statistical average value between 0 and 10,
u is equal to 0 or 1, with the restriction that when $u=0$, s and r are also zero,
R denotes
(i) a linear or branched hydrocarbon radical which has 1 to 32 carbon atoms and can contain one or more oxygen atoms in the chain or bear one or more OH groups or
(ii) a ($C_8$-$C_{18}$ alkyl)phenyl radical.

These compounds can be used for preparing stable chemical compounds, for conveying active substances or for forming vesicles.

11 Claims, No Drawings

NEW HEMIACETAL COMPOUNDS AND THE APPLICATIONS THEREOF

This application is a division of application Ser. No. 07/340,754, filed Apr. 20, 1989 (now U.S. Pat. No. 5,008,406), which is a division of application Ser. No. 06/874,006, filed Jun. 13, 1986 (now U.S. Pat. No. 4,827,003).

The invention relates to new compounds bearing a cyclic hemiacetal group, the preparation thereof and their use in organic synthesis for preparing well defined chemical compounds, or in mixtures, or in chemical technology in various industries such as cosmetics, pharmaceuticals, medical diagnosis, textiles, agriculture, and the like.

In the chemical industry, it is important to be able to have available compounds which are both reactive and stable.

The Applicant has discovered new compounds, forming the subject of the present invention, which possess these advantages and are reactive towards a large number of chemical compounds or various substrates (fibres, resins, powders, sheets, etc.) bearing amine, thiol, hydroxyl, etc., groups.

These compounds can be used for preparing stable chemical compounds, or alternatively be employed to convey "active substances" with which they react, forming a labile covalent bond, thereby enabling these active substances to be released under special conditions. Some of these compounds can be used to form vesicles in an aqueous medium.

The products according to the invention are essentially characterized in that they correspond to the formula:

$$R-(O)_u-A-(CH_2)_m \diagup \begin{matrix} O-(CH_2)_q \\ (CH_2)_n-O-(CH_2)_p \end{matrix} \diagdown \begin{matrix} OH \\ H \end{matrix} \quad (I)$$

in which:
m, n, p and q are equal to 0 or 1, p being different from q and the sum $m+n+p+q=2$, A denotes a nonionic chain arrangement chosen from the groups $-C_2H_4O_r$ and/or $-C_3H_5(OH)O]_s$, r denotes a number which can assume all integral values between 0 and 5 or a statistical average value between 0 and 20, s denotes a number which can assume all integral values between 0 and 5 or a statistical average value between 0 and 10, u is equal to 0 or 1, with the restriction that when u is zero, s and r are also zero, R denotes:
(i) a linear or branched hydrocarbon radical which contains from 1 to 32 carbon atoms and can contain one or more oxygen atoms in the chain or bear one or more hydroxyl groups,
(ii) an alkylphenyl radical in which the alkyl radical contains 8 to 18 carbon atoms.

The group $-C_3H_5(OH)O-$ denotes the following 3 structures:

$$-CH_2-CH-O-; \quad -CH_2-CHOH-CH_2O-;$$
$$\phantom{-CH_2-}|\phantom{CH-O-}$$
$$\phantom{-CH_2-}CH_2OH$$

-continued $$-CH-CH_2O-$$
$$\phantom{-}|$$
$$CH_2OH$$

Two compounds are regarded as isomers when the indices r and/or s have the same integral value and in which:

either the groups $-C_3H_5(OH)O-$ described above are different in structure, or the heterocyclic systems containing the hemiacetal group of formula (I) are different in structure, or both of these together.

The mixtures of homologous compounds, that is to say the compounds having various degrees of polymerization in which r and/or s have a statistical average value, or possibly having different hydrocarbon chain lengths, also form part of the invention.

The hemiacetal derivatives of the invention are obtained by oxidation with periodic acid, or its sodium salt ($NaIO_4$), of (poly)glycerol ethers containing a terminal 2,3-dihydroxypropyl ether group and, in addition, a third hydroxyl group in the $\beta$- or $\gamma$-position to the ether group.

The (poly)glycerol ethers which can be used in the process according to the invention can be represented by the formulae below:

$$R-O-A-\left[CH_2-CH-O\right]_2-H \quad (IIA)$$
$$\phantom{R-O-A-[}|\phantom{CH-O]}$$
$$\phantom{R-O-A-[}CH_2OH$$

$$R-O-A+CH_2-CHOH-CH_2O\}_2H \quad (IIB)$$

$$R-O-A-CH-CH_2-O-CH_2-CHOH-CH_2OH \quad (IIC)$$
$$\phantom{R-O-A-}|$$
$$\phantom{R-O-A-}CH_2OH$$

$$R-CHOH-CH_2-O-CH_2-CHOH-CH_2OH \quad (IID)$$

$$R-CH-O-CH_2-CH-CH_2OH \quad (IIE)$$
$$\phantom{R-}|\phantom{-O-CH_2-}|$$
$$\phantom{R-}CH_2OH\phantom{-O-CH_2}OH$$

in which R and A have the meanings stated above.

The preparation of the hemiacetals according to the invention can be illustrated schematically by the following reactions:

Reaction A $$R-O-A-CH_2-CH-O-CH_2-CHOH$$
$$\phantom{R-O-A-CH_2-}|\phantom{-O-CH_2-}|$$
$$\phantom{R-O-A-CH_2-}CH_2OH\phantom{-O-CH_2}CH_2OH$$

$$HIO_4 \downarrow$$

$$R-O-A-CH_2-CH-O-CH_2-C\diagup^O_H + HC\diagup^O_H$$
$$\phantom{R-O-A-CH_2-}|$$
$$\phantom{R-O-A-CH_2-}CH_2OH$$

$$\downarrow \text{cyclization}$$

-continued

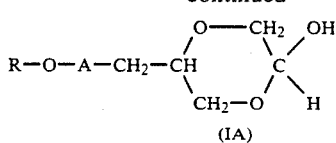
(IA)

Reaction B

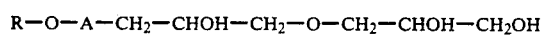

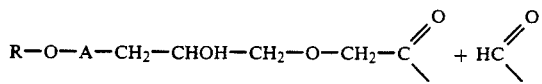

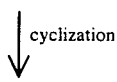

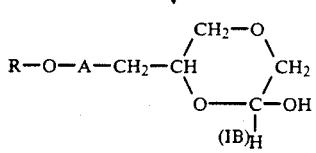
(IB)

Reaction C

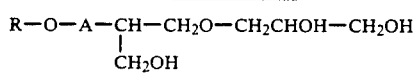

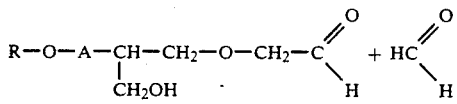

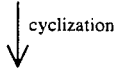

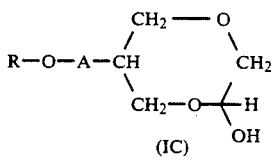
(IC)

Reaction D

R—CHOH—CH₂—OCH₂—CHOH—CH₂OH

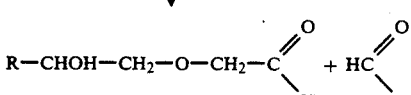

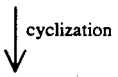

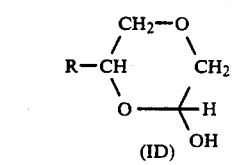
(ID)

Reaction E

-continued

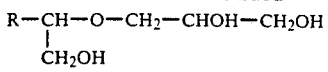

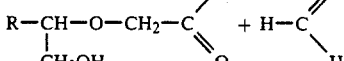

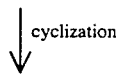

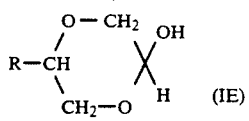
(IE)

The mixtures of polyglycerol ethers which are used in the process according to the invention can contain small proportions of monoglycerol ethers not possessing the third OH group in the β- or γ-position to the ether group. These compounds are oxidized to an ether of ethanal, the presence of which is not detrimental, and they can be removed if necessary.

The polyglycerol ethers required for the synthesis of the products of the invention are prepared according to known processes. They can be prepared, in particular, from alcohols ROH or (poly)ethoxylated alcohols of formula R-O-(C₂H₄O)$_r$ in which R and r have the meanings stated above, according to the following processes;

On an alcohol, a mixture of alcohols, a (poly)ethoxylated alcohol or a mixture of polyethoxylated alcohols, there is performed a (poly)addition of:

either epichlorohydrin, followed by hydrolysis, as described in French Patents 1,477,048 and 2,465,780;

or tert-butyl glycidyl ether, followed by hydrolysis, as described in French Patent 2,087,785;

or allyl glycidyl ether, followed by purification to isolate the monoaddition product and finally hydroxylation, as described in French Patent 1,484,723.

The glycerol ethers of formula (IID) and (IIE) are obtained according to conventional means, for example by addition of glycerin or its derivatives to an epoxide.

The hemiacetals are prepared from the (poly)glycerol ethers which correspond to the definitions given above.

The (poly)glycerol ethers may be used:
either in the state of a single pure product,
or in the state of a mixture of isomers,
or in the state of a mixture of isomers and homologues.

The pure products, isomers and homologues are defined as stated above.

The pure hemiacetals are either obtained from the pure (poly)glycerol ethers, or are isolated from mixtures by distillation, preparative HPLC (high pressure liquid chromatography) or any other process.

The oxidation reaction of the (poly)glycerol ethers is performed carrying out prior solubilization of the starting compounds in water or in an alcohol such as methanol, ethanol or isopropanol, in proportions varying from 5 to 30% of active material. To this solution, metaperiodic acid or its sodium salt, to which has been added its own weight of water, is added at a temperature of between 10° and 80° C., and preferably between 20° and 40° C., in the proportion of 1 to 1.1 mole per terminal —CHOH—CH₂OH group of compound(s)

IIA, IIB, IIC, IID or IIE. Agitation is maintained for a period ranging from rather less than an hour to several hours. The excess periodic acid and the iodic acid formed are removed either by washing with water or by gel filtration or filtration on silica.

The hemiacetal compounds according to the present invention are characterized especially by their reactivity towards alcohols, amines, thiols, basic amino acids, proteins, polymers bearing primary amine groups, and the like.

They can react with primary amines such as $(C_1-C_{18})$-alkylamines, arylalkylamines such as benzylamine, and primary amines having alcohol group(s), especially monoethanolamine, diglycolamine, tris(hydroxymethyl)aminomethane, 2-amino-2-methyl-1,3-propanediol and glucamine.

The reaction with amines is conducted at room temperature in a solvent such as water or methanol. A Schiff's base is obtained, which is reduced by reducing agents such as $NaBH_4$ or $NaBH_3CN$, and this reaction can lead to compounds represented by the following general formulae:

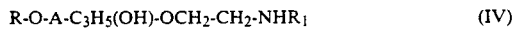

$$R\text{-}O\text{-}A\text{-}C_3H_5(OH)\text{-}OCH_2\text{-}CH_2\text{-}NHR_1 \qquad (IV)$$

when the starting hemiacetal has the formula IA, IB or IC, or $$R\text{-}CHOH\text{-}CH_2\text{-}O\text{-}CH_2\text{-}CH_2NHR_1 \qquad (IV')$$

when the starting hemiacetal has the formula ID, in which R and A have the same meaning as above and $R_1$ denotes the primary amine residue.

The hemiacetals according to the invention can also be reacted with primary/tertiary diamines such as dimethylaminoethylamine, dimethylaminopropylamine, diethylaminoethylamine or diethylaminopropylamine.

The hemiacetals defined above also react with natural or synthetic polymers bearing primary amine groups and having a molecular weight of less than or equal to 1,000,000, such as chitosan, polyethyleneimines and polyvinylamines.

Other compounds having an amine group which are capable of reacting with the hemiacetals are chosen from amino acids such as lysine, proteins such as, for example, trypsin, glutathione, polylysine, or immunoglobulins of the IgG type or other antibodies.

The hemiacetals according to the invention can also be made to react with mercaptans $R_2SH$, where $R_2$ denotes a $C_1-C_{18}$ alkyl radical or a $C_1-C_{18}$ mono- or polyhydroxyalkyl radical such as, for example, thioethanol or thioglycerol. Sulphur amino acids $R_2\text{-}SH$, where $R_2$ denotes the amino acid residue, such as, for example, cisteine, can also be reacted.

In this case, the reaction is performed at between 30° and 70° C. in solvents such as methanol or ethanol, and is catalysed by hydrochloric acid. In this case, depending on the proportion of the reagents, it is possible to obtain thiohemiacetals represented by the general formula:

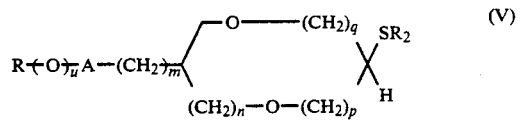

(V)

in which R, A, m, n, p, q and u have the meanings stated in connection with the formula (I) and $R_2$ denotes the residue of the thiol.

The reaction with the abovementioned thiols can also lead to dithioacetals represented by the formulae:

$$R\text{-}O\text{-}A\text{-}C_3H_5(OH)CH_2\text{-}CH(SR_2)_2 \qquad (VI)$$

when the starting hemiacetal has the formula IA, IB or IC, or $$R\text{-}CHOH\text{-}CH_2\text{-}O\text{-}CH_2\text{-}CH(SR_2)_2 \qquad (VI')$$

when the starting hemiacetal has the formula ID, in which formulae R and A have the same meaning as stated above and $R_2$ denotes the residue of the thiol.

The hemiacetals of formula (I) can also react with linear or branched alcohols of formula $R_3OH$, where $R_3$ denotes a $C_1-C_{18}$ hydrocarbon radical.

In this case, the reaction is performed at a temperature of between 30° and 70° C. and is catalysed by acids such as sulphuric acid or Lewis acids such as $BF_3$. In this case, acetals are obtained corresponding to the formula:

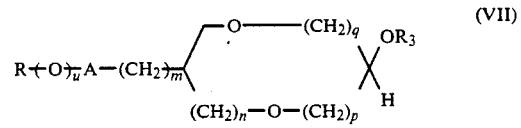

(VII)

in which R, A, m, n, p, q and u have the meanings stated above and $R_3$ denotes the residue of the alcohol.

As alcohols, $C_1-C_{18}$ monohydric alcohols such as, for example, ethanol, butanol or dodecanol may be mentioned.

The hemiacetals of formula (I) can also react with phenols or alkylphenols of formula $R_4OH$, where $R_4$ denotes an optionally substituted phenyl radical or an alkylphenyl radical, under conditions similar to those described for the reaction with alcohols. Acetals are obtained of formula VIII:

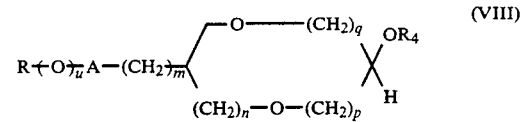

(VIII)

in which R, A, m, n, p, q and u have the meanings stated above and $R_4$ denotes the residue of the phenol. As phenols, phenol, resorcinol, octylphenol and nonylphenol may be mentioned.

The compounds according to the invention can also undergo a reduction reaction, such as with, for example, sodium borohydride $(NaBH_4)$, to lead to alcohols corresponding to the formulae:

$$R\text{-}O\text{-}A\text{-}C_3H_5(OH)\text{-}O\text{-}CH_2\text{-}CH_2OH \qquad (IX)$$

when the starting hemiacetal has the formula IA, IB or IC, or $$R\text{-}CHOH\text{-}CH_2\text{-}O\text{-}CH_2\text{-}CH_2OH \qquad (IX')$$

when the starting hemiacetal has the formula ID.

The compounds resulting from the various reactions described above, and represented in particular by the formulae IV, IV', V, VI, VI', VII, VIII, IX and IX', are new and constitute a further subject of the invention.

These compounds or mixtures of compounds can find various applications.

When the hemiacetals which are the subject of the invention bear a long aliphatic chain, for example containing at least 12 carbon atoms, they possess surfactant properties and can be dispersable or soluble in water depending on the values of r and s. Among the products which are dispersable in water, some possess, in particular, the property of forming vesicles or liposomes.

These products generally take the form of spherules dispersed in an aqueous medium, and consist of multimolecular layers, and preferably of bimolecular layers having an approximate thickness of 30 to 100 Å [see in particular the paper by Bangham, Standish and Watkins, J. Mol. Biol., 13, 238 (1965)]. For the sake of simplicity, the term liposome will be used to designate this type of product.

The liposomes can be obtained, in particular, according to the process described in the Applicant's French Patent No. 2,315,291, according to which a dispersion of spherules consisting of organized molecular layers enclosing an aqueous phase is prepared by bringing into contact, on the one hand a hemiacetal or a mixture of hemiacetals of formula (I), in which R denotes a group preferably having at least 12 carbon atoms, and on the other hand the aqueous phase to be encapsulated in the said spherules, agitating to ensure mixing and obtain a lamellar phase, then adding a dispersion liquid in an amount greater than the amount of lamellar phase obtained and shaking vigorously for a period varying between 15 minutes and 3 hours approximately.

The ratio by weight between the aqueous phase to be encapsulated, brought into contact with the hemiacetals according to the invention, and the hemiacetals forming the lamellar phase is between approximately 0.1 and approximately 3.

The ratio by weight of the dispersion phase, which is added, to the lamellar phase, which is dispersed, is preferably between approximately 2 and approximately 100, the dispersion phase and the aqueous phase to be encapsulated preferably being isoosmotic.

The dispersion phase is an aqueous solution containing, where appropriate, active substances.

The agitation is carried out by means of a shaker and the process can be performed at room temperature or at a higher temperature, depending on the nature of the hemiacetal. It is also possible to subject the dispersion of spherules to ultrasound treatment when it is desired to obtain liposomes having a mean diameter of less than 1000 Å.

Another preparation process can consist in using the process known as REV (reverse-phase evaporation vesicle), described in Proc. Natl. Acad. Sci. USA, Vol. 75 No. 9 p. 4194–4198 (1978) by Szoka and Papahadjopoulos.

Various additives can be incorporated for the purpose of modifying the permeability or the surface charge of the liposomes.

To this end, mention may be made of long-chain alcohols and diols, sterols, for example cholesterol, long-chain amines and their quaternary ammonium derivatives, dihydroxylamines, polyoxyethylenated fatty amines, long-chain esters of amino alcohols, their salts and quaternary ammonium derivatives, phosphoric acid esters of fatty alcohols, alkyl sulphates or other lipids of the type defined in French Patent No. 2,315,991 and more especially lipids containing a saturated or unsaturated, branched or linear lipophilic chain from 12 to 30 carbon atoms long, such as, for example, oleic, lanolic, tetradecyl, hexadecyl, isostearyl, lauric or alkylphenyl chains. The hydrophilic group of these lipids can be an ionic or nonionic group. By way of nonionic groups, groups derived from polyethylene glycol may be chosen. When the hydrophilic group of the lipid which forms the lamellar phase is an ionic group, an amphoteric, anionic or cationic compound can be chosen, for example, as lipids having a hydrophilic group. Polyglycerol ethers such as those described in French Patents Nos. 1,477,048, 2,091,516, 2,465,780 and 482,128 can thus be used.

As is well known, the aqueous phase to be encapsulated can be water or an aqueous solution of active products such as, for example, substances having pharmaceutical, foodstuff of nutrient value, or substances having cosmetic activity.

As regards substances having cosmetic activity, it is possible, for example, to use products intended for skin care and hair care such as, for example, humectants such as glycerin, sorbitol, pentaerythritol, inositol, pyrrolidonecarboxylic acid and its salts; artificial suntan agents such as dihydroxyacetone, erythrulose, glyceraldehyde, γ-dialdehydes such as tartaraldehyde, optionally combined with colourings; water-soluble anti-sunburn agents, antiperspirants, deodorants, astringents, freshening-up products, tonics, healing products, keratolytics, depilatories; scented waters; extracts of animal and plant tissues such as proteins, polysaccharides, amniotic fluid; water-soluble colourings, antidandruff agents, antiseborrheic agents, oxidizing agents such as bleaching agents, for example hydrogen peroxide, and reducing agents such as thioglycolic acid and its salts.

As active pharmaceutical substances, vitamins, hormones, enzymes such as superoxide dismutase, vaccines, anti-inflammatories such as hydrocortisone, antibiotics, bactericides, cytotoxic agents or antitumour agents may be mentioned.

A subject of the invention consists of liposomes or spherules in dispersion, obtained using at least one hemiacetal of formula I and having a diameter of between $0.1\mu$ and $5\mu$.

An especially advantageous application of the liposomes defined above is the reaction at their surface with compounds or products bearing alcohol, thiol or amine groups, and formation of a covalent bond.

In the case of reactions with compounds or products bearing amine groups, the reaction may be followed by reduction with reducing agents such as $NaBH_4$ and $NaBH_3CN$ to form a covalent bond between the product bearing amine groups and the liposome.

Usable products bearing amine groups can be proteins preferably containing lysyl residues, especially at least 20 lysyl radicals. To this end, immunoglobulins such as IgG may be mentioned.

An advantageous application of this type of reaction is the coupling of specific antibodies or monoclonal antibodies with liposomes containing cytotoxic substances or substances capable of modifying the behaviour of a cell. The antibodies are then capable of specifically directing the liposomes and their contents to the target cells.

Another application is in methods of medical diagnosis such as, for example, in a method for visualizing haemagglutination in the determination of Rhesus factor by means of an antibody-antigen interaction.

The examples which follow are intended to illustrate the invention without thereby being limitative in nature.

EXAMPLE 1

Preparation of compounds I, II and III.

A mixture of polyhydroxypropylene ether compounds:

$$C_{16}H_{33}O-[CH_2CHO-]_n-H$$
$$\quad\quad\quad\quad\quad |$$
$$\quad\quad\quad\quad\quad CH_2OH$$

n having an average statistical value of approximately 3, is prepared according to French Patent 1,477,048.

232 g of the abovementioned mixture are solubilized in 2.5 of methanol. 126 g of metaperiodic acid, to which its own weight of water has been added, is added to this solution in the course of half an hour and at room temperature. The reaction mixture is agitated for 3 hours. 2 liters of water are then added.

Copious precipitation of a white solid is observed.

Is is collected by centrifugation and then washed three times with 200 cc of boiling water.

After being dried, 200 g of a product of waxy appearance, very slightly tinted yellow and melting below 50° C., are isolated.

This product is a statistical mixture of hemiacetal derivatives. The pure compounds are isolated by subjecting the above mixture to preparative high pressure liquid chromatography (HPLC).

The chromatography conditions are as follows: Sample: 67 g solubilized in 100 cc of dichloromethane. Phase: 1 kg of Merck 60 H Kieselgel (silica gel 60 H, sold by Merck).

Compression of the phase: 9 bars.
Eluent: dichloromethane/methanol=85:15.
Elution pressure: 9 bars.

The following are isolated: 26 g, 13 g and 6 g, respectively, of the compounds I, II and III.

Compound I $$C_{16}H_{33}OCH_2-\underset{O}{\overset{O}{\diagup}}\!\!\!\diagdown\!\!\!\underset{H}{\overset{OH}{\diagup}}$$

White solid of melting point 70° C.
Elementary analysis:

|   | Calculated | Found |
|---|---|---|
| C | 70.34 | 70.07 |
| H | 11.81 | 11.76 |

IR: Stretching C-O 1150, 1120 and 1065 cm$^{-1}$; absence of C=O band

The $^{13}$C NMR spectrum accords with the structure of the compound I.

Compound II $$C_{16}H_{33}OCH_2CHOCH_2-\underset{O}{\overset{O}{\diagup}}\!\!\!\diagdown\!\!\!\underset{H}{\overset{OH}{\diagup}}$$
$$\quad\quad\quad\quad |$$
$$\quad\quad\quad\quad CH_2OH$$

White solid of melting point 56° C.
Elementary analysis:

|   | Calculated | Found |
|---|---|---|
| C | 66.63 | 66.7 |
| H | 11.18 | 11.2 |

The $^{13}$C NMR spectrum accords with the above structure.

Mass spectroscopy on silylated derivative OH=OSi(CH$_3$)$_3$ M$^+$ −15=561.

Compound III $$C_{16}H_{33}O-[CH_2CHO-]_2-CH_2-\underset{O}{\overset{O}{\diagup}}\!\!\!\diagdown\!\!\!\underset{H}{\overset{OH}{\diagup}}$$
$$\quad\quad\quad\quad\quad |$$
$$\quad\quad\quad\quad\quad CH_2OH$$

White solid of melting point 50° C.
Elementary analysis:

|   | Calculated | Found |
|---|---|---|
| C | 64 | 64.41 |
| H | 10.74 | 10.8 |

EXAMPLE 2

PREPARATION OF THE COMPOUND OF THE FORMULA $$CH_3CH_2CH_2(CH_2)_{12}CH_2OCH_2-\underset{O}{\overset{O}{\diagup}}\!\!\!\diagdown\!\!\!\underset{H}{\overset{OH}{\diagup}}$$

To 521 g (2.15 moles) of molten hexadecanol, there are added 18.38 g of a solution of sodium methylate in methanol (5.82 meq/g) 164 g (1.43 moles) of ally glycidyl ether are then added at 150° C. and in the course of 1 h 30 min, and agitation is maintained for a further 1 hour. The product is then washed with boiling water until neutral, and then distilled at 0.01 mm Hg. 128 g are collected of a liquid fraction which distils at 172° C. and which consists of a single product:

$$C_{16}H_{33}OCH_2CHOHCH_2OCH_2CH=CH_2$$

This compound is subjected to hydroxylation as described in French Patent 1,531,010, to obtain the derivative:

$$C_{16}H_{33}OCH_2CHOHCH_2OCH_2CHOHCH_2OH$$

126 g of the above compound are dissolved in 2 liters of methanol. 82 g of metaperiodic acid, to which its own weight of water has been added are added to this solution in the course of half an hour and at room temperature.

The reaction mixture is agitated for 3 hours. The formation of a precipitate is observed. To enhance the precipitation, 2 liters of water are added. The solid is drained, taken up with 2 liters of chloroform and washed with 3 times 200 cc of water. After the product is dried, there are collected 104 g of a compound of formula:

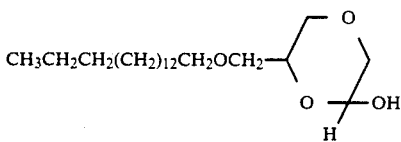

This is a white solid of melting point 92° C.
Elementary analysis:

|   | Calculated | Found |
|---|---|---|
| C | 70.34 | 70.28 |
| H | 11.81 | 11.8 |

The $^{13}$C NMR spectrum accords with the above structure.

EXAMPLE 3

Preparation of a Mixture of the Following Compounds

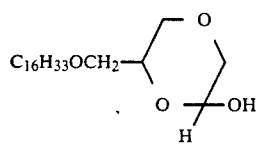

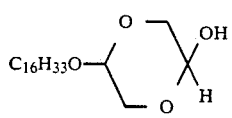

1.8 cm³ of BF$_3$.Et$_2$O is added to 403 g (1.66 mol) of molten hexadecanol, and the mixture is brought to 70° C. At this temperature, 190 g (1.66 mol) of allyl glycidyl ether are added in the course of 1 hour, and heating is maintained for 1 hour. The mixture is washed several times with boiling water and then distilled at 0.01 mm Hg. 228 g are collected of a fraction which distils at 175° C. and which contains the two compound:

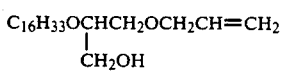

This mixture is subjected to hydroxylation as described in French Patent 1,531,010, to obtain the derivatives:

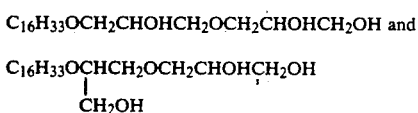

50 g of the above mixture are dissolved in 700 cm³ of methanol. The solution is treated under the same conditions as in Example 2 with 31 g of metaperiodic acid to which its own weight of water has been added. After 3 hours' agitation, 700 cm³ of water are added. The solid formed is drained, taken up with 700 cm³ of chloroform and washed with 3 times 75 cm³ of water. After being dried, 40 g of a mixture of the following compounds are collected:

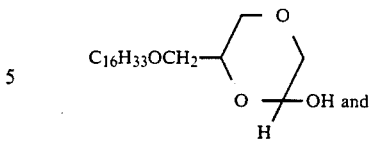

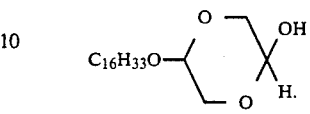

This is a white solid of melting point 83° C.
Elementary analysis:

|   | Calculated | Found |
|---|---|---|
| C | 70.34 | 70.62 |
| H | 11.81 | 11.85 |

In gas chromatography, this mixture shows two peaks, the more abundant of which is superposed with the peak of the compound of Example 2.

Mass spectroscopy shows that the two compounds have indeed the same mass: M+ −18=340.

IR spectroscopy shows the absence of the characteristic aldehyde band.

EXAMPLE 4

Preparation of the Thioacetals of Formulae:

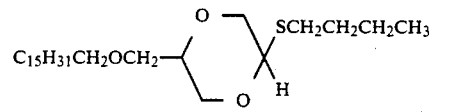

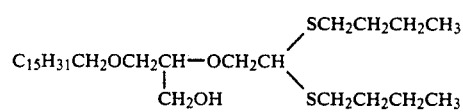

1.79 g (0.005 mol) of the hemiacetal (I) prepared according to Example 1 is dissolved in 25 cm³ of absolute ethanol. 3 cm³ of ethanol saturated with HCl are added to this solution, followed by 0.9 g (0.01 mol) of butylmercaptan. The mixture is agitated for 10 hours at room temperature. It is evaporated to dryness.

The solid is taken up with hexane and washed several times with water. The mixture obtained is subjected to preparative HPLC (same conditions as in Example 1, but with dichloromethane as eluent).

On the one hand, 0.3 g is isolated of a thioacetal of formula:

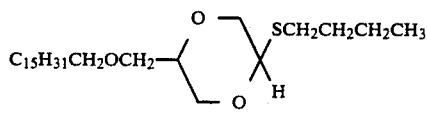

The $^{13}$C NMR spectrum accords with this structure.

On the other hand, 0.5 g is isolated of a dithioacetal of formula:

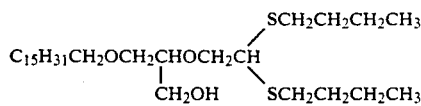

The $^{13}C$ NMR spectrum accords with this structure.

EXAMPLE 5

Preparation of the Thioacetal of Formula

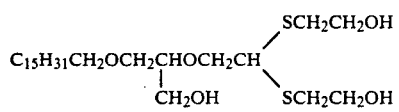

3.58 g (0.01 mol) of hemiacetal (I) prepared according to Example 1 are dissolved in 50 cm$^3$ of a solution of HCl in methanol (2.6N). 1.95 g (0.025 mol) of mercaptoethanol dissolved in 30 cm$^3$ of methanol is added to this solution. The solution is heated for 6 hours at 50° C. and then evaporated to dryness. The mixture is subjected to preparative HPLC (same conditions as in Example 1, but with the eluent dichloromethane/isopropanol, 90:10).

1.5 g of a pasty solid is isolated. This is the dithioacetal:

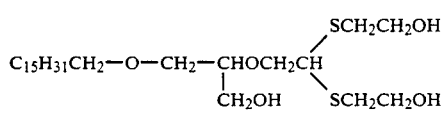

Le $^{13}C$ NMR spectrum accords with this structure.
Elementary analysis:

|   | Calculated | Found |
|---|---|---|
| C | 60.48 | 60.57 |
| H | 10.48 | 10.5 |
| S | 12.9 | 12.66 |

EXAMPLE 6

Preparation of the compound of formula

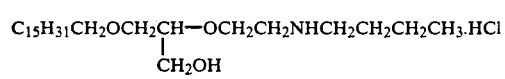

2 g (0.006 mol) of hemiacetal (I) prepared according to Example 1 are dissolved in 55 cm$^3$ of methanol. 0.41 g (0.006 mol) of butylamine is added to this solution. The mixture is agitated at room temperature. A precipitation is observed and this becomes enhanced with the passage of time. After 4 hours' agitation at room temperature, 1.85 g of a white solid is isolated by filtration.

1 g of this solid is redissolved in 30 cm$^3$ of methanol. 0.092 g (0.0024 mol) of sodium borohydride is added to this solution and the mixture is agitated for 3 hours at room temperature. 1 drop of acetic acid is then added. The mixture is evaporated to dryness. The residue is taken up with dichloromethane and the solution washed with water.

After evaporation of the organic phase, the solid is redissolved in ether to which a few cm$^3$ of ether saturated with HCl are added.

By precipitation, 0.7 g is isolated of a white solid of melting point 100° C. and of formula:

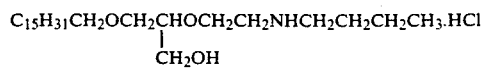

The $^{13}C$ NMR spectrum accords with the above structure.

EXAMPLE 7

Preparation of the compound of formula

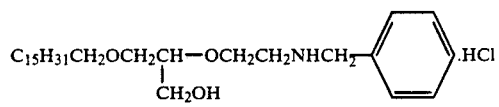

3.58 g (0.01 mol) of the hemiacetal (I) prepared according to Example 1 are dissolved in 100 cm$^3$ of methanol. 1 cm$^3$ of normal sulphuric acid solution is added to this solution, followed by 1.07 g (0.01 mol) of benzylamine.

The solution is agitated at room temperature. A solid precipitates during the reaction. After 3 hours' agitation, it is isolated by filtration.

2.24 g of this solid are redissolved in 300 cm$^3$ of methanol. 0.185 g of sodium borohydride is added and agitation is maintained for 1 h 30 min. 1 drop of acetic acid is then added. The mixture is evaporated to dryness. The solid is taken up with dichloromethane. The organic solution is washed with water. After evaporation of the dichloromethane, an oil is collected. This oil is redissolved in ether. A white solid is precipitated by adding a few cm$^3$ of ether saturated with HCl. 1.7 g of a white solid, of melting point 105° C., is isolated.

Its acid value is 2.22 meq/g. The $^{13}C$ NMR spectrum accords with the following structure:

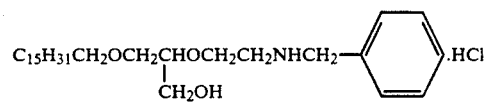

EXAMPLE 8

Preparation of the Two Isomers

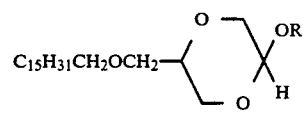

OR: axial and equatorial
OR: OCH$_2$(CH$_2$)$_8$-CH$_2$CH$_2$CH$_3$ 2 g (0.0056 mol) of hemiacetal (I) prepared according to Example 1 are dissolved in 40 cm$^3$ of tetrahydrofuran, followed by 2.08 g (0.011 mol) of dodecanol. 16 mg of BF$_3$.Et$_2$O are added to this solution, which is then brought for 8 hours to 70° C.

The solvent is evaporated off and the solid subjected to HPLC, as in Example 1 but on Lichroprep Si 60 and with the system hexane/ethyl acetate (9:1) as eluent.

2 g of a white solid, of melting point 58° C., are isolated.

This is a mixture of the two isomers below:

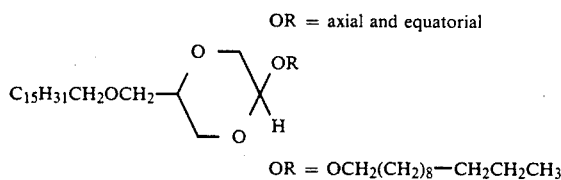

OR = axial and equatorial
OR = OCH₂(CH₂)₈—CH₂CH₂CH₃

The ¹³C NMR spectrum accords with the above structure.

Elementary analysis

|   | Calculated | Found |
|---|------------|-------|
| C | 74.65 | 74.55 |
| H | 12.92 | 13.01 |

EXAMPLE 9

Preparation of the Compounds of Formulae (I) and (II)

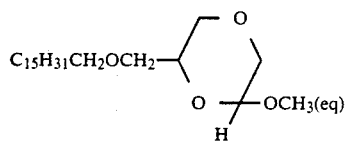 (I)

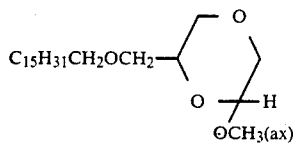 (II)

3 g (0.0084 mol) of hemiacetal prepared according to Example 2 are dissolved in 30 cm³ of methanol. 10 drops of H₂SO₄ (N) are added and the solution is heated for 3 hours to 60° C. The solution is then evaporated to dryness. The solid is taken up with dichloromethane and washed with water. The mixture is evaporated to dryness. 2 g of solid are obtained and this is subjected to HPLC as in Example 1, with dichloromethane as eluent. 2 fractions are isolated. One of these, of 0.3 g, contains the pure compound:

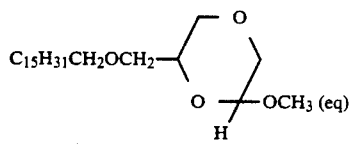 (I)

The other fraction, of 1.5 g, contains a mixture of the compound (I) and the compound (II):

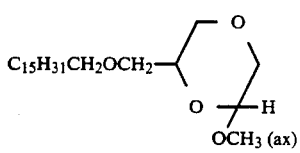 (II)

Elementary analysis:

|   | Calculated | Found |
|---|------------|-------|
| C | 70.92 | 70.79 |
| H | 11.90 | 12.01 |

Melting point: 58° C.

Mass spectroscopy: the two compounds show the same molecular peak M⁺−32 (loss of methanol)=340

The ¹³C NMR spectra accord with the structures of the compounds I and II.

EXAMPLE 10

Preparation of the Compound of Formula

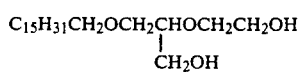

1 g (0.0028 mol) of hemiacetal (I) prepared according to Example 1 is dissolved in 50 cm³ of methanol. 0.1 g (0.0026 mol) of sodium borohydride is added to this solution. The mixture is stirred for 1 h 30 min at room temperature. 1 drop of acetic acid is added.

The mixture is evaporated to dryness. The residue is taken up with dichloromethane. The mixture is washed with water. 0.87 g are isolated of a white solid of melting point 66° C. and structure:

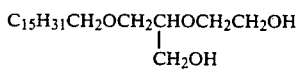

confirmed by the ¹³C NMR spectrum.

EXAMPLE 11

Preparation of the compound of Formula:

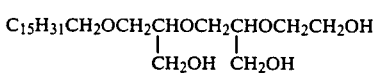

0.5 g (0.016 mol) of hemiacetal (II) prepared according to Example 1 is dissolved in 45 cm³ of methanol, and 0.04 g (0.0011 mol) of sodium borohydride is then added. Agitation is maintained for 3 hours at room temperature. 1 drop of acetic acid is added. The mixture is evaporated to dryness. The residue is taken up with dichloromethane and the mixture washed with water. 0.3 g is obtained of a pasty compound melting at about 50° C., of structure:

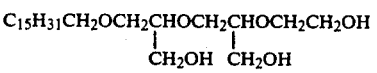

confirmed by the ¹³C NMR spectrum.

Mass spectroscopy: silylated derivative with OH-=OSi(CH₃)₃ peak M⁺+H=651.

EXAMPLE 12

Preparation of a Dispersion of Active Vesicles

The starting materials are the following products: di(hydroxypropylenoxy) derivative C₁₆H₃₃O(CH₂CHO)₂—H: 1.188 g;
|
CH₂OH hemiacetal II prepared according to Example 1: 1.188 g;
cholesterol: 2.375 g;
dicetyl phosphate: 0.25 g;
aqueous solution containing 0.02% of NaN₃: 95 g.

Procedure 95 g of an aqueous solution of NaH₃ are added slowly and with manual agitation to the 5 g of molten lipids (60°-80° C.). The dispersion formed is made finer by ultradispersion (Polytron 20,000 rpm) followed by sonication.

The dispersion obtained, which is stable for several months, consists of non-flocculated mono- or multilamellar vesicles, the average diameter of which, measured using a Coulter N4 counter (Coultronics), is between 100 and 150 nm, and the surface potential (Zeta potential) of which, measured using a Zmeter 501 laser, is in the region of −60 mV.

Reaction of the Vesicles with Protein

The vesicle dispersion is diluted with a borate buffer solution (10 mM Na₂B₄O₇, 60 mM NaCl, 3 mM NaN₃) to a final concentration of 20 mg of lipids/ml of dispersion.

4 ml of solution of Sigma trypsin—60% pure—(20 mg/ml of buffer solution) is added to 4 ml of this dispersion in the course of 10 min with agitation.

The mixture is adjusted to pH 9.5 by adding N NaOH and left agitated at room temperature for approximately 2 hours. 60 μl of freshly prepared NaBH₄ solution (10% strength in the buffer) are then added [equivalent to 3.6 moles of NaBH₄ per mole of hemiacetal of formula (II)].

The mixture is agitated for 1 hour and then left standing overnight at room temperature.

The vesicles and the free trypsin are separated by filtration on a Sephadex G-200 column (sample deposition 3 ml, eluent borate buffer pH 8.4, ascending elution, flow rate 0.5 ml/min).

The vesicles obtained have an average diameter of between 100 and 200 nm and contain approximately 9 mg of trypsin per g of lipids.

EXAMPLE 13

Preparation of the Four Isomers

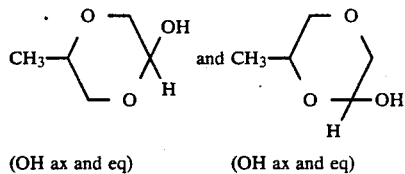

(OH ax and eq)   (OH ax and eq)

46 g (0.8 mol) of propylene oxide are added dropwise in the course of 1 hour to 211 g (1.6 mol) of freshly distilled isopropylideneglycerol containing 0.6 ml of BF₃ etherate, the temperature being maintained at 60°±5° C.

After the acidity due to the catalyst has been neutralized with 1.16 ml of sodium methylate dissolved in methanol (6 meq/g), the excess isopropylideneglycerol is distilled off under a vacuum of 30 mm of mercury, the residue is then fractionated by distillation under a vacuum of 0.1 mm of Hg and 40 g of a colourless liquid which distils at 70°-72° C. are collected. This liquid is composed of the two isomers of the formulae below:

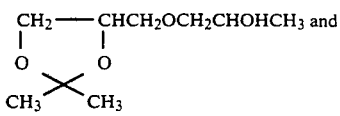

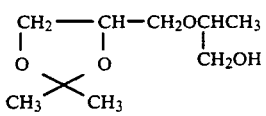

1 ml of concentrated hydrochloric acid diluted in 2 ml of water is added to 19 g (0.1 mol) of the mixture of the above compounds dissolved in 50 ml of methanol. The solution is left for 3 days at room temperature and then concentrated under a vacuum of 25 mm Hg at 80° C.

14 g are isolated of a colourless oil showing a single spot in TLC on silica (eluent CH₂Cl₂/CH₃OH, 90:10), corresponding to a mixture of the two isomers:

CH₃—CHOH—CH₂—O—CH₂—CHOH—CH₂OH and

CH₃—CH—O—CH₂—CHOH—CH₂OH
|
CH₂OH

A solution of 40 g of periodic acid (at HIO₄.2 H₂O) dissolved in 150 ml of water is added to 24 g (0.16 mol) of a product obtained according to the above procedure, dissolved in 100 ml of water, the temperature being maintained at 25°-30° C. during the addition; the mixture is then agitated at room temperature for 5 hours.

The iodic acid formed is then neutralized with a suspension of 30 g of barium hydroxide [Ba(OH)₂.8 H₂O] in 100 ml of water, the temperature being maintained at a maximum of 35° C. The mixture is left agitated for 2 hours and then filtered on No. 4 sintered glass. The filtrate is concentrated to dryness under a vacuum of 25 mm of Hg in a bath at 50° C. The residue is taken up with 30 ml of isopropanol, the mixture filtered again and the filtrate concentrated as above. 17 g of a colourless oil are obtained. This product is purified by preparative chromatography under pressure (Merck Silica Gel 60 H, eluent dichloromethane/isopropanol: 95:5).

12 g are isolated of a colourless mobile oil which shows a single spot in TLC. By gas chromatography of the silylated mixture on a 15-m capillary column OV 1701, four compounds are distinguished which have been identified as isomers by mass spectroscopy (M⁺−H=189).

The ¹³C NMR spectrum accords with the presence of the four isomers below:

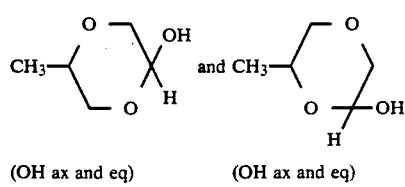

(OH ax and eq)   (OH ax and eq)

EXAMPLE 14

Preparation of the Compound Having the Structure:

$$C_{14}H_{25}-\underset{C_{10}H_{21}OCH_2}{CHO}-\left[\underset{CH_2OH}{CH_2CHO}\right]_{n'}-CH_2CH\underset{O}{\overset{O}{\diagdown}}\underset{OH}{\overset{H}{\diagup}}$$

where n' has an average statistical value of 2.

A mixture of the polyhydroxypropylene ether compounds of formula:

$$\underset{C_{14}H_{25}-CH-O}{\overset{C_{10}H_{21}-O-CH_2}{|}}-\left[CH_2-\underset{CH_2OH}{\overset{|}{CH}}-O\right]_n-H$$

where n has an average statistical value of 4, is prepared according to French Patent BF 2,465,780.

5 g of periodic acid (HIO$_4$.2 H$_2$O) dissolved in 6 ml of water are added to 6.94 g (0.01 mol) of the above derivative dissolved in 400 ml of methanol, and the mixture is left agitated for 12 hours at room temperature. The solution is then brought down to 100 ml by partial evaporation of the solvent under reduced pressure. An equal amount of water is added at 80° C. to this concentrated solution. An oil appears in the mixture and phase separation occurs.

After separation, the aqueous phase is washed several times with heptane. The organic extracts are combined with the oil and dried over sodium sulphate. After removal of the sodium sulphate and evaporation of the solvent, 6.2 g of a viscous oil are isolated.

The $^{13}$C NMR spectrum accords with the structure below:

$$\underset{C_{14}H_{25}-CHO}{\overset{C_{10}H_{21}OCH_2}{|}}-\left[CH_2-\underset{CH_2OH}{\overset{|}{CHO}}\right]_{n'}-CH_2-CH\underset{O}{\overset{O}{\diagdown}}\underset{OH}{\overset{H}{\diagup}}$$

where n' has an average statistical value of 2.

We claim:

1. A process for manufacturing a dispersion of liposomes consisting of organized molecular layers enclosing an aqueous phase, comprising:
   a) bringing a hemiacetal or a mixture of hemiacetals corresponding to the formula:

$$R(O)_uA-(CH_2)_m\diagup\overset{\displaystyle O-(CH_2)_q}{\underset{\displaystyle (CH_2)_n O-(CH_2)_p}{\diagdown}}\diagup\overset{OH}{\underset{H}{\diagdown}} \quad (I)$$

in which m, n, p and q are equal to 0 or 1, p being different from q and the sum m+n+p+q being equal to 2, A denotes a nonionic chain arrangement chosen from the groups:

$(C_2H_4O)_r$ and/or $[C_3H_5(OH)O]_s$ in which r denotes a number which can assume all integral values between 0 and 5 or a statistical average value between 0 and 20, s denotes a number which can assume all integral values between 0 and 5 or statistical average value between 0 and 10, u is equal to 0 or 1, with the restriction that when u is equal to 0, s and r are also zero, R denotes (i) a linear or branched hydrocarbon radical which has 12 to 32 carbon atoms and can contain one or more oxygen atoms in the chain or bear one or more OH groups, or (ii) a (C$_8$–C$_{18}$ alkyl)phenyl radical, and the hemiacetal or mixture of hemiacetals may additionally comprise an ether of ethanal; into contact with an aqueous phase to be encapsulated in the said liposomes;

b) agitating the resulting mixture to ensure mixing and to obtain a lamellar phase, c) adding a dispersion liquid in an amount greater than the amount of lamellar phase obtained, and d) shaking the thus-obtained mixture vigorously.

2. Liposomes obtained by the process of claim 1 and having a diameter of between approximately 0.1μ and 5μ.

3. Liposomes according to claim 2 in the encapsulated aqueous phase and further comprising at least one substance having cosmetic, pharmaceutical or foodstuff activity.

4. Liposomes according to claim 3 in which the substance having cosmetic activity comprises at least one product selected from the group consisting of humectant, artificial suntan agent, water-soluble anti-sunburn agent, antiperspirant, deodorant, astringent, freshening-up product, tonic, healing product, keratolytic, depilatory, scented water, extract of animal or plant tissue, water-soluble colouring, antidandruff agent, antiseborrheic agent, oxidizing agent and reducing agent.

5. Liposomes according to claim 4 in which the humectant is a member selected from the group consisting of glycerin, sorbitol, pentaerythitol, inositol and pyrrolidonecarboxylic acid or a salt thereof; the artificial suntan agent is a member selected from the group consisting of dihydroxyacetone, erythrulose, glyceraldehyde and a γ-dialdehyde.

6. Liposomes according to claim 3 in which the substance having pharmaceutical activity comprises at least one product selected from the group consisting of vitamin, hormone, enzyme, vaccine, anti-inflammatory, antibiotic, bactericides, cytotoxic agent and antitumor agent.

7. Liposomes according to claim 2 wherein the hemiacetal or mixture of hemiacetals of formula (I) is combined or in admixture with long-chain alcohol, diol, sperol, long-chain amine, long-chain amine quaternary ammonium derivatives, dihydroxylamine, polyoxyethylenated fatty amine, long-chain ester of amino alcohol, a salt or quaternary ammonium derivative thereof, phosphoric acid ester of fatty alcohol, alkyl sulphate or lipid containing a saturated or unsaturated branched or linear lipophilic chain of from 12 to 30 carbon atoms long for the purpose of modifying the permeability or the surface charge of the said liposomes.

8. A process comprising reacting a compound or product bearing an alcohol, thiol or amine group at the surface of the liposomes according to claim 2.

9. A process according to claim 7, further comprising reacting protein containing lysyl residues with the liposomes of claim 42.

10. A process according to claim 8 further comprising coupling a monoclonal antibody with the liposomes.

11. A product comprising liposomes according to claim 3 bound covalently to a protein.

* * * * *